(12) United States Patent
Boven et al.

(10) Patent No.: US 12,214,194 B2
(45) Date of Patent: *Feb. 4, 2025

(54) OPTIMIZATION TOOL FOR AUDITORY DEVICES

(71) Applicant: Soundwave Hearing, LLC, Glendale Heights, IL (US)

(72) Inventors: Christopher L. Boven, Chicago, IL (US); Reagan John Roberts, Barrington, IL (US)

(73) Assignee: Soundwave Hearing, LLC, Glendale Heights, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/223,369

(22) Filed: Jul. 18, 2023

(65) Prior Publication Data

US 2024/0017065 A1 Jan. 18, 2024

Related U.S. Application Data

(63) Continuation of application No. 17/566,819, filed on Dec. 31, 2021, now Pat. No. 11,701,516, which is a continuation of application No. 15/832,536, filed on Dec. 5, 2017, now Pat. No. 11,213,680.

(60) Provisional application No. 62/430,062, filed on Dec. 5, 2016.

(51) Int. Cl.
*A61N 1/36* (2006.01)
*H04R 25/00* (2006.01)
*A61N 1/05* (2006.01)

(52) U.S. Cl.
CPC ....... *A61N 1/36038* (2017.08); *H04R 25/505* (2013.01); *H04R 25/70* (2013.01); *A61N 1/0541* (2013.01); *A61N 1/36039* (2017.08); *H04R 2225/41* (2013.01); *H04R 2225/67* (2013.01)

(58) Field of Classification Search
CPC .............. A61N 1/36038; A61N 1/0541; A61N 1/36039; H04R 25/505; H04R 25/70; H04R 2225/41; H04R 2225/67; H04R 1/1083
See application file for complete search history.

(56) References Cited

U.S. PATENT DOCUMENTS

2015/0382106 A1* 12/2015 Kraft ..................... H04W 4/021
381/119

* cited by examiner

*Primary Examiner* — Tammie K Marlen
(74) *Attorney, Agent, or Firm* — K&L Gates LLP (57) ABSTRACT

A system comprises an auditory device processor, an auditory device output mechanism, an auditory input sensor, a database including a reference bank of environmental sounds and corresponding sound profiles, and a memory. The auditory device processor is configured to: while the auditory input sensor is detecting a first environmental sound, receive a sound selection from the user, wherein the sound selection is associated with the first environmental sound; store a first sound profile in the reference bank corresponding to the first environmental sound; receive a second environmental sound detected by the auditory input sensor; analyze a frequency content of the second environmental sound; compare the frequency content of the second environmental sound with the reference bank of environmental sounds and corresponding sound profiles stored in the database; in response to the comparison, select one of the sound profiles corresponding to the second environmental sound; and automatically adjust the parameter settings.

19 Claims, 7 Drawing Sheets

OPTIMIZATION TOOL FOR AUDITORY DEVICES

CROSS-REFERENCE TO RELATED APPLICATIONS

This application is a continuation application of U.S. application Ser. No. 17/566,819 filed Dec. 31, 2021 (now U.S. Pat. No. 11,701,516), which is a continuation application of U.S. application Ser. No. 15/832,536 filed Dec. 5, 2017 (now U.S. Pat. No. 11,213,680), which claims the benefit of priority to U.S. Provisional Application No. 62/430,062, filed on Dec. 5, 2016, the entireties of which have been incorporated by reference.

BACKGROUND OF THE INVENTION

The present invention relates systems and methods for optimizing parameters of hardware for audiological devices. More specifically, the present invention relates to systems and methods in which acoustic waves are transformed into electrical signals in a device, and the settings of the device are tailored to the individual.

Programming hardware for audio signals is complicated due to the complexity of audio signals. In addition to the basic problems associated with reproducing a constantly changing sound comprised of an overlapping collection of various pitches and amplitudes, problems are compounded by signal to noise issues, threshold hearing variances across a wide range of the spectrum in which humans can hear, and other unique factors. With such a complex variable set, or from another perspective, such a wide optimization space, it is difficult for a user or operator to arrive at an optimized setting.

For example, cochlear implants include technology that transforms complex auditory waves into pulses to be sent to a plurality of channels on the inner cochlea of a patient in order to stimulate the neurons on the select channels. The process of transforming auditory waves into electronic signals requires the transformation of a multitude of information including frequency, amplitude, and voltage among background noise and environments into an electrical signal to recreate hearing.

Cochlear implants are neural prostheses that help severely-to-profoundly deaf people to restore some hearing. Physically, three components can be identified: the speech processor with its transmission coil, the receiver and stimulator, and the cochlear implant electrode array. The speech processor receives sound from one or more microphones and converts the sound into a corresponding electrical signal. While the hearing range of a young healthy human is typically between 0.02 and 20 kHz, it has been assumed for coding of acoustic information in cochlear implants that most of the information used for communication is in the frequency range between 0.1 and 8 kHz. The frequency band from 0.1 to 8 kHz is divided into many smaller frequency bands of about 0.5 octaves width. The number of small frequency bands is determined by the number of electrodes along the electrode array, which is inserted into the cochlea. Each frequency band is then treated by a mathematical algorithm, such as a Hilbert transform that extracts the envelope of the filtered waveform. The envelope is then transmitted via an ultrahigh frequency (UHF) connection across the skin to a receiver coil, which was surgically implanted behind the ear. The envelope is used to modulate a train of pulses with a fixed pulse repetition rate. For each of the electrodes, a train of pulses with fixed frequency and fixed phase is used to stimulate the cochlear nerve. Multiple algorithms have been implemented to select a group of 4-8 electrode contacts for simultaneous stimulation.

Damage of cochlear neural structures can result in severe deafness. Depending on the neural degeneration in the cochlea performance, the performance of a cochlear implant user may vary. Changes that occur include the demyelination and degeneration of dendrites and neuronal death. The neuronal loss can be non-uniform and results in "holes" of neurons along the cochlea. Holes lead to distortion of the frequency maps, which affects speech recognition. Caused by changes in myelination and synapse size, changes in firing properties of the nerve were described such as prolonged delay times and changed refractory periods. In the brainstem and midbrain the neuronal connections appear to remain intact. However, a decrease in neuron size, afferent input, synapse size and density can be detected. Neural recordings reveal a change in response properties that adversely affect temporal resolution such as elevated thresholds, de-synchronization, increased levels of neural adaptation, increased response latencies. A loss of inhibitory influences has been described. At the cortex, spatially larger cortical activation was seen with (PET). The findings support a plastic reorganization and more intense use of present auditory networks.

A conventional cochlear implant includes a speech processor that transforms the acoustic waves received on the microphone into an electrical signal that stimulate the implanted electrode array, and consequently, the auditory nerves. Auditory waves are a complex summation of many different wave forms, and the processor decomposes the complex auditory signal received on the microphone into discrete component frequencies or electrical pulses to be sent to the auditory neurons through the electrodes. Nerve fibers in the vicinity of the electrodes are stimulated and relay information to the brain. Loud sounds produce high-amplitude electrical pulses that stimulate a greater number of nerve fibers, while quiet sounds produce low-amplitude pulses effected a lesser number of nerve fibers. Different variables within the software on the processor affect the output of the cochlear implant speech processor.

To activate the cochlear implant, an audiologist tunes the levels and stimulation parameters of the speech processor so that the sounds picked up by the microphone are heard at the individual's ideal loudness level. Initially, the audiologist stimulates the implant's channels or electrode pairs with small electrical pulses to test whether the user hears the stimulus. Over the course of subsequent sessions, the audiologist performs a series of tests to understand the user's listening needs. The user's cochlea is tuned to perceive different pitches depending on the area being stimulated. During the sessions, the audiologist stimulate the implant's channels to simulate pitch differences. The audiologist will also vary the electrical current on each channel to find the most comfortable loudness level. The audiologist may also take threshold measurements to understand the user's softest level audible on each channel. The audiologist ultimately generates a map that is downloaded to the speech processor to enable the processor to appropriately adjust volume levels based on the individual's needs.

With cochlear implants and other hearing devices, each patient is unique. Following implantation, changes occur that can affect performance of the device. Changes include genetic disorders, iatrogenic procedures, ototoxic drugs, or loud noise exposure. The user's hearing will change over time, requiring additional visits to the audiologist in order to rerun the tests and adjust the map accordingly.

Additionally, hearing devices other than cochlear implants, such as recent hearing aid technology, may require programming based on audiological feedback during testing to achieve optimal results. The latest generations of hearing aids and other "hearables" include parameter settings for amplification, compression, noise rejection/cancellation, etc. Being able to fine tune each of the parameters, in each ear, provides even greater flexibility in the optimization of these devices. However, the complexity created by the many parameters can be a challenge for manual tuning.

Accordingly, there is a need for an optimization system for effectively adjusting a large number of parameters of a hearing device while accounting for a variety of hearing situations.

SUMMARY OF THE INVENTION

The optimization system of the present application allows a patient to intuitively define parameter settings for a large number of parameters in association with a variety of environments. The optimization system includes a first module, a second module, and a third module. It is understood that the first through third modules may be integrated into a single program or be provided in a fewer or greater number of modules. The first module collects and analyzes a wide range of patient feedback as input data to determine ranges for each parameter tailored to the cochlea of the patient. The second module includes a plurality of user interfaces that prompt the patient to select a preferred set of data point(s) corresponding to a specific pitch and/or frequency. The data points initially provided to the patient in the second module are within the specific ranges provided as output from the first module. Within the second module, one or more user interfaces allow the patient to compare a large number of parameter settings against one another in a single trial.

The third module includes a database on which a reference bank of sounds or environments that identify frequency content associated with each acoustic environment is stored. Using wavelet scattering transforms, a classifier algorithm determines the frequency content of each acoustic environment. Alternative methods such as traditional Fourier transforms or spectrograms may be used. Support vector machine (SVM), K-clustering mechanisms, or any type of clustering methods is used to group the information contained in each acoustic environment to create a reference bank of sounds (i.e., noisy restaurant, beach, and metro station).

In one embodiment, a system for controlling parameter settings of an auditory device includes: an auditory device processor; an auditory device output mechanism controlled by the auditory device processor, the auditory device output mechanism including one or more modifiable parameter settings; an auditory input sensor that detects an environmental sound and communicates with the auditory device processor; a database in communication with the auditory device processor, the database pairing each of a plurality of sets of parameter settings with a corresponding sound profile; a memory in communication with the processor and including instructions that, when executed by the processor, cause the processor to: receive the environmental sound detected by the auditory input sensor; analyze a frequency content of the environmental sound; compare the frequency content of the environmental sound with the sound profiles stored in the database and, in response to the comparison, select one of the sound profiles; and automatically adjust the parameter settings of the auditory device output mechanism to match the set of parameter settings associated with the selected sound profile.

In some embodiments, when the auditory device processor analyzes a frequency content of the environmental sound it uses a wavelet scattering transform to analyze the frequency content of the environmental sound. In other embodiments, when the auditory device processor analyzes a frequency content of the environmental sound it uses a Fourier transform to compute the frequency content of the environmental sound.

In some embodiments of the systems herein, the sound profiles are clustered by similarities. The frequency content of the environmental sound may include one or more properties selected from the group comprising a signal-to-noise ratio, an amplitude range, and a pitch range. The one or more properties selected from the group comprising a signal-to-noise ratio, an amplitude range, and a pitch range of the frequency content of the environmental sound matches the corresponding one or more properties selected from the group comprising a signal-to-noise ratio, an amplitude range, and a pitch range of one of the sound profiles.

In some examples of the system, the auditory device output mechanism is an electrode of a cochlear implant and the auditory input sensor is microphone of a cochlear implant.

In some examples of the system, the auditory device output mechanism is speaker of a hearing aid and the auditory input sensor is microphone of a hearing aid.

Each set of the plurality of sets of parameter settings may include amplification settings, compression settings, and directional noise rejection settings.

In some examples of the system, each sound profile is associated with a stored geolocation, the system further comprises a location sensing mechanism in communication with the auditory device processor, and when the processor compares the frequency content of the environmental sound with the sound profiles stored in the database and, in response to the comparison, selects one of the sound profiles, the processor further compares a present geolocation of the auditory device output mechanism identified by the location sensing mechanism with the stored geolocations.

An objective of the present design is to provide a user-friendly optimization system for adjusting a variety of parameters of a hearing device. In some examples, the hearing device is a cochlear implant. In other examples, the hearing device is a hearing aid. In other examples, the hearing device is another hearable device.

An objective is to provide a system for automatically controlling parameter settings of an auditory device such that the device automatically updates its settings in response to recognizing the auditory environment in which it is being used.

An objective is to improve the performance of auditory devices across a wide range of audio environments by enabling real-time adaptation of the setting of the device.

Additional objects, advantages and novel features of the examples will be set forth in part in the description which follows, and in part will become apparent to those skilled in the art upon examination of the following description and the accompanying drawings or may be learned by production or operation of the examples. The objects and advantages of the concepts may be realized and attained by means of the methodologies, instrumentalities and combinations particularly pointed out in the appended claims.

BRIEF DESCRIPTION OF THE DRAWINGS

The foregoing and other objects, features, and advantages of the present disclosure set forth herein will be apparent from the following description of particular embodiments of those inventive concepts, as illustrated in the accompanying drawings. Also, in the drawings the like reference characters refer to the same parts throughout the different views. The drawings depict only typical embodiments of the present disclosure and, therefore, are not to be considered limiting in scope.

DETAILED DESCRIPTION

The present application provides an optimization system that optimizes the parameters of an auditory device based on the individual's specific needs to improve the user's ability to hear.

Figure 1:
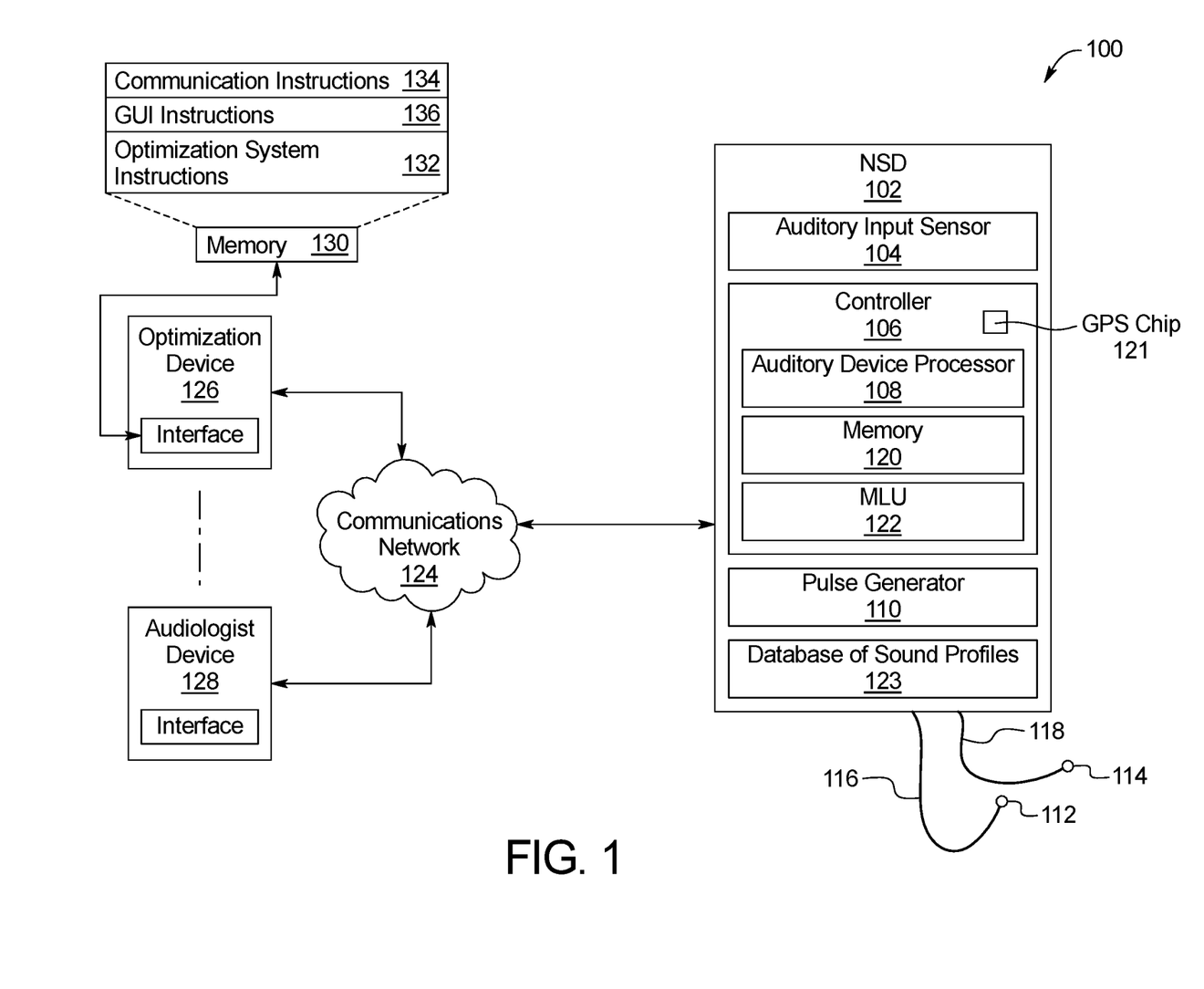
FIG. 1 is a schematic illustrating the components of the optimization system of the present disclosure in use with a cochlear implant.

FIG. 1 is a block diagram illustrating an example system 100 for performing various activities involving the activation, modulation, and/or blockage of neurons within the brain using an audio device such as a cochlear implant or hearing aid. As illustrated, the system 100 includes a neurostimulation device (NSD) 102. The NSD 102 may be implantable (e.g., below the skin), or alternatively, may be some type of external device, such as a cochlear implant device or a hearing aid device. Primary example used herein is a cochlear implant, although the system 100 may apply to a hearing aid or other hearable device.

In the example shown in FIG. 1, the NSD 102 transforms acoustic waves into electrical impulses. An auditory input sensor 104 such as a microphone on the NSD 102 captures the acoustic wave, and a controller 106 including an auditory device processor 108 deconstructs the acoustic wave and utilizes a pulse generator 110 to generate discrete electrical pulses that are then provided to an auditory device output mechanism such as an electrode array on the cochlea. Specifically, the pulse generator 110 generates electrical impulses ("pulses") in specific patterns for electrical stimulation of nervous tissue of the cochlea. Stated differently, the pulses generated by the pulse generator 110 are applied in specific patterns to specific regions and/or portions of the nervous system to deliver neurostimulation. The pulse generator 110 may be electrically coupled to electrodes 112 and 114 via one or more leads 116 and 118, respectively, and thereby provide neurostimulation to the specific regions of the nervous system. The pulses generated by the pulse generator 110 are conducted through the one or more leads 116 and 118 and terminated in the electrodes 112 and 114 generally implanted in the tissue of the nervous system. In another embodiment where the auditory device is a hearing aid, the auditory device output mechanism may be a speaker.

The auditory device processor 108 on the controller 106 controls the pulse generator 110 to deliver electrical pulses (i.e., neurostimulation) according to a selected stimulation parameter set (e.g., pulse amplitude, pulse width, pulse frequency, etc.) and/or other instructions to applicable regions of the nervous system. Neurostimulation programs or coding strategies based on variable parameters that are used in the delivery of neurostimulation therapy (i.e., stimulation) may be stored in a memory 120, in the form of executable instructions and/or software, for execution by the auditory device processor 108. The auditory device or NSD 102 may also include a global positioning system (GPS) chip 121 and a database of reference sound profiles 123, which may be utilized in the programming stored on the memory 120 as described below.

In some embodiments, the controller 106 may contain a machine-learning logic unit ("MLU") 122 that is trained to perform machine-learning operations involving the generation of various predictions that may be used to optimize the functionality of the NDS 102 and/or initiate and optimize neurostimulation therapy provided to a patient via the NDS 102. The MLU 122 may process data received from users interacting with the NDS 102 when generating such predictions. Although the controller 106 is illustrated as being included within the NSD 102, in some embodiments, it may be implemented in a computing device that is separate from the NDS 102. In such an embodiment, the controller 106 may communicate with the NSD 102 remotely, such as through a communications network 124, which may be a telecommunications network, the Internet, an intranet, a local area network, a wireless local network, radio frequency communications protocol, or any other type of communications network, as well as combinations of networks.

The NSD 102 may be communicatively connected to an optimization device 126 and/or an audiologist device 128 locally or via the communications network 124 to receive input that may be processed to optimize neurostimulation therapies and/or optimal functions of the NDS 102. Each of the optimization device 126 and the audiologist device 128 provides user interface(s) that enable a patient or user to provide the input (e.g., data) to the NSD 102 that defines, qualifies, and/or quantifies aspects of the neurostimulation therapy provided by the NDS 102. More specifically, variables of the equations that are part of computer program stored in the memory 120 of the NSD 102 are set by the optimization interface and/or the audiologist interface of the optimization device 126 and the audiologist device 128, respectively. Each of the devices 126, 128 may include a processor-based platform that operates on an operating system, such as Microsoft® Windows®, Linux®, iOS®, Android®, and/or the like that is capable of executing and/or otherwise generating the interfaces.

The user or operator of the optimization device 126 works with the patient wearing the NSD 102 to gather user feedback in response to audio tests as shown in FIGS. 4-8 and described below. The user interfaces of the optimization device 126 can be coupled to memory 130 that can store program instructions 132 to run the optimization system. Further, the memory 130 may also store communication instructions 134 to facilitate communicating with one or more additional devices, one or more computers, and/or one or more servers. The memory 138 may include graphical user interface instructions 136 to facilitate graphic user interface processing.

The audiologist operates the device 128 to directly adjust the programming or instructions on the memory 120 of the NSD 102. Specifically, the audiologist may provide input in the form of a set of stimulation parameters that define various parameters, such as pulse amplitude, pulse width, pulse frequency, etc., any of which may be used to automatically determine a specific neurostimulation therapy (e.g., parameter space) for a particular patient. Based on such input, the controller 106 logically directs the pulse generator 110 to modify internal parameters and vary the characteristics of stimulation pulses transmitted to the nervous system. The audiologist may interact with the optimization device 126 to provide feedback regarding the success of the simulation (e.g., better, same, or worse) in comparison to previous neurostimulation therapies, to modify parameters of the current simulation, etc.

Each of the above identified instructions and applications can correspond to a set of instructions for performing one or more functions described herein. These instructions need not be implemented as separate software programs, procedures, or modules. The memory 130 can include additional instructions or fewer instructions. Furthermore, various functions of the system 100 may be implemented in hardware and/or in software, including in one or more signal processing and/or application specific integrated circuits.

In one example, the memory 120 includes stored instructions that, when executed by the auditory device processor 108, cause it to deconstruct acoustic waves into discrete electrical signals and to generate electrical pulses through the pulse generator. In one example, U.S. Pat. No. 9,717,901 discloses a frequency-modulated phase coding (FMPC) strategy to encode acoustical information in a cochlear implant 102. The entirety of the disclosure provided by U.S. Pat. No. 9,717,901 is incorporated herein. The FMPC strategy utilizes the following equation that describes the relationship between the sound level at the outer ear canal and the corresponding rate of action potentials that can be recorded from a single auditory nerve fiber. This function is expressed below and includes cochlear nonlinearities and depends on five critical parameters: a spontaneous rate ($a_0$), a maximum rate ($a_1$), a threshold for stimulation ($a_2$), a level for nonlinear behavior ($a_3$), and a value describing the slope after the level for nonlinear behavior ($a_4$).

$$R = a_0 + \frac{a_1 * d^2}{a_2^2 + d^2},$$

where R is the mean discharge rate, and d is $$d = \left[ \frac{a_3^{\left(\frac{1}{a_4}-1\right)} * p^{\frac{1}{a_4}}}{a_3^{\left(\frac{1}{a_4}-1\right)} + p^{\left(\frac{1}{a_4}-1\right)}} \right]^{a_4}$$

where the variables denote the following:
$a_0$=the spontaneous discharge rate of the primary afferent,
$a_1$=the maximum increase of the discharge rate,
$a_2$=the sound pressure of the half maximum discharge rate,
$a_3$=the sound pressure at which nonlinear behavior occurs,
$a_4$=the exponent of the power-law slope in the nonlinear region, p the sound pressure level at the tympanic membrane, and
p=10*log 10(abs(S1(frequency))), where S1 is the Short Time Fourier Transform (STFT) of the acoustic signal.

Each of FIGS. 3A-3E illustrates the mean discharge rate R having various values of the parameters $a_0$, $a_1$, $a_2$, $a_3$, $a_4$. Values of each parameter per graph of FIGS. 3A-3E are provided in Table 1 below.

TABLE 1

Figure 3A:
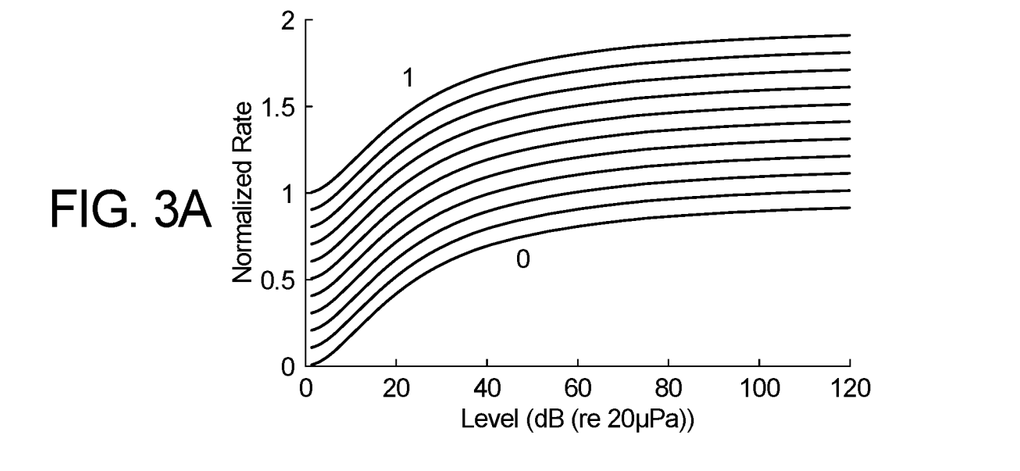
FIGS. 3A-3E are charts illustrating the potential variance provided by modifying the parameters of an example coding strategy of a cochlear implant that may be used with the optimization system of FIG. 1.
Figure 3B:
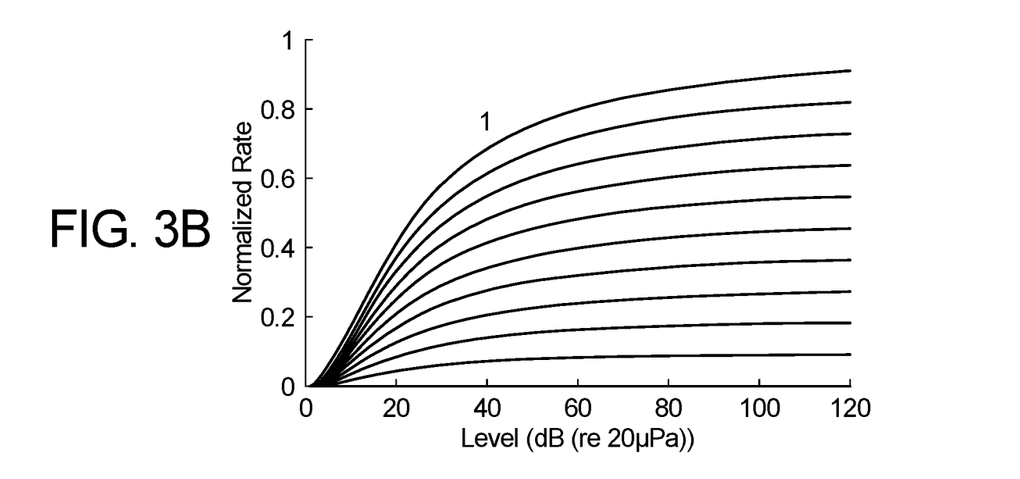
Figure 3C:
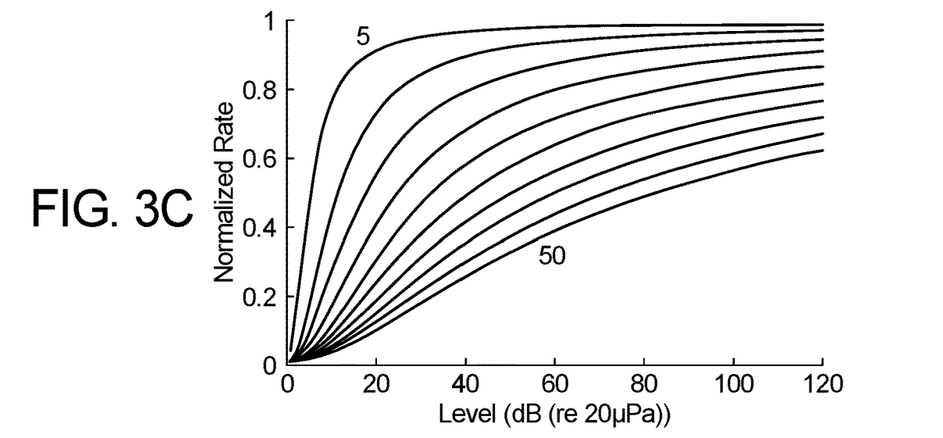
Figure 3D:
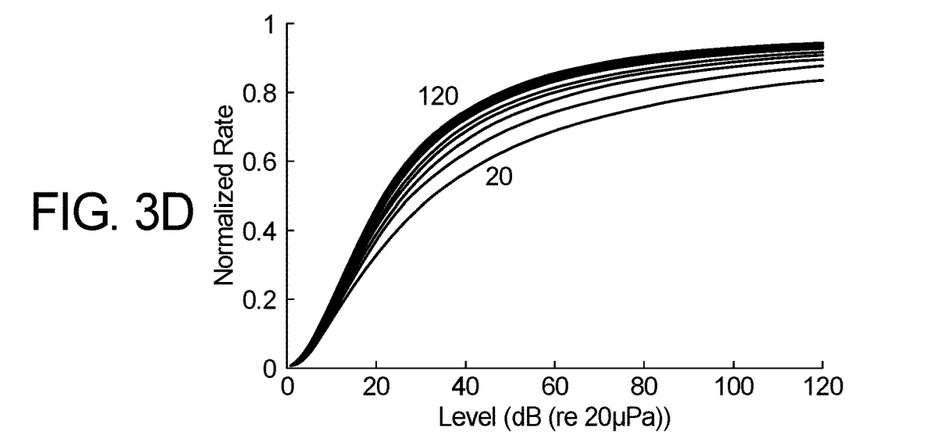
Figure 3E:
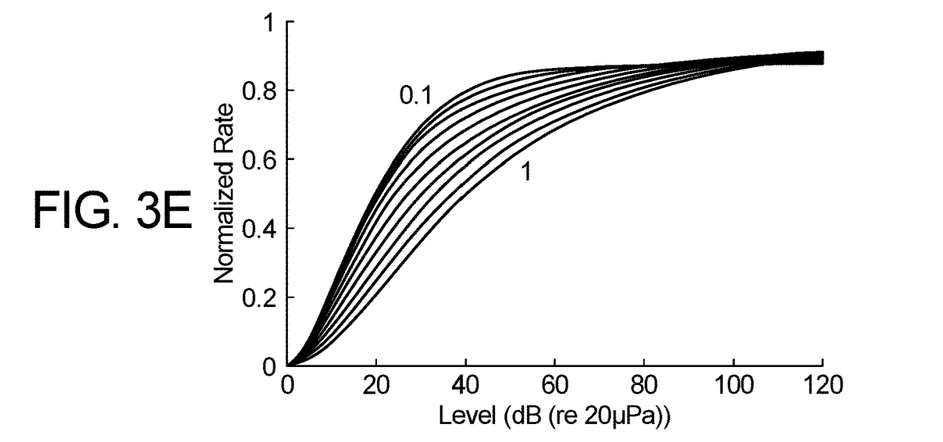

| Parameter values for FIGS. 3A-3E | | | | | |
|---|---|---|---|---|---|
| | $a_0$ | $a_1$ | $a_2$ | $a_3$ | $a_4$ |
| FIG. 3A | 0:0.1:1 | 1 | 20 | 50 | 0.5 |
| FIG. 3B | 0 | 0:0.1:1 | 20 | 50 | 0.5 |
| FIG. 3C | 0 | 1 | 5:5:50 | 50 | 0.5 |
| FIG. 3D | 0 | 1 | 20 | 20:10:120 | 0.5 |
| FIG. 3E | 0 | 1 | 20 | 50 | 0.1:0.1:1 |

Traces in FIG. 3A show that the spontaneous discharge rate $a_0$ shifts the curve towards larger values. The maximum rate $a_1$ limits the maximum rate to the number selected (FIG. 3B). The level for threshold $a_2$ has large effects on the mapping. Low threshold values result in a fast increase in the rate and quick saturation whereas large threshold values slow the increase in rate but limit the maximum in achievable rate (FIG. 3C). Smaller effects are seen from the parameters $a_3$ and $a_4$ (FIGS. 3D and 3E). Default values are selected ($a_0$=0, $a_1$=1; $a_2$=20; $a_3$=50, and $a_4$=0.5), which must be adjusted individually during later sessions with the CI user.

The above variables are examples of the types parameters that are adjusted during the audiologist tuning sessions. Any hearing device can have more or fewer parameters noted above depending on the coding strategy.

In the systems of the present application, the optimization system 200 is used to optimize the values of the parameters of the coding strategy programmed on the memory 120 of the NSD 102. In the primary example provided, the optimization system 200 is described as being embodied in first, second, and third modules 202, 204, 206. It is understood that any one or more of the three modules 202, 204, 206 can be used independently or in any combination to describe the features and functions described herein. It is also understood that all three modules 202, 204, 206 could be a single system, independent systems, or combinations thereof.

Figure 2:
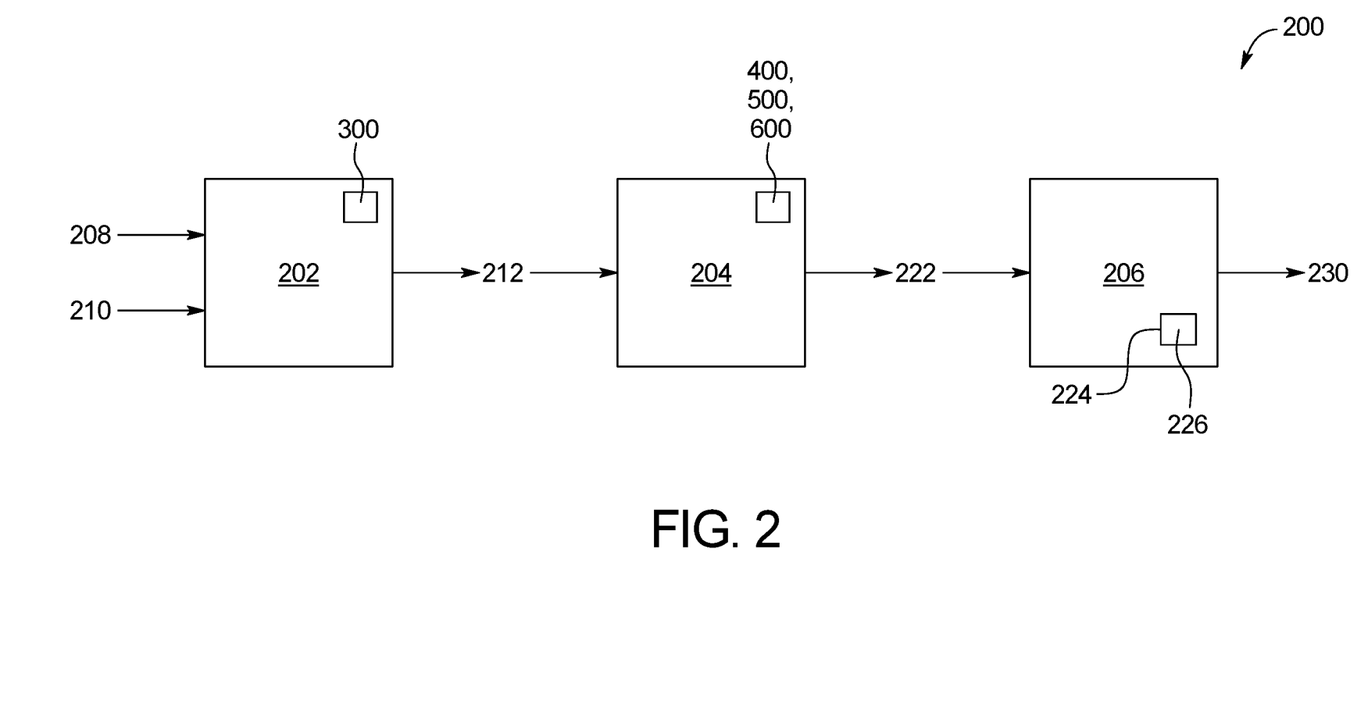
FIG. 2 is a block diagram illustrating the interaction between the first, second, and third modules of the optimization system of FIG. 1.

Referring to FIG. 2, the first module 202 collects and analyzes a wide range of patient feedback 208 as input data to determine ranges for each parameter tailored to the cochlea of the patient. The memory 130 on the optimization device 126 includes stored instructions that, when executed, cause it to prompt the patient to identify threshold decibel levels 210 under a plurality of conditions. In one embodiment, the plurality of conditions includes first through fifth conditions described below, although any number and/or types of conditions may be used to effectuate the desired thresholds.

The first condition determines the patient's threshold for detecting speech. A sound is provided to the patient and gradually increases in volume. The patient indicates when he or she first detects the noise against a quiet background.

The second condition determines the patient's preference for the most comfortable decibel level. A sound bite of speech is provided to the patient and gradually increases in volume. The patient indicates when he or she first understands the speech clearly at a comfortable level, such as listening to an audiobook.

The third condition determines the patient's threshold for recognizing speech. A sound bite of speech is provided to the patent at a high decibel level and gradually decreases in volume. The patient indicates when he or she can no longer understand what is being said.

The fourth condition determines the patient's threshold for the most uncomfortable decibel level. A sound bite of speech is provided to the patient and gradually increases in volume. The patient indicates when the speech reaches a level that it is uncomfortable to hear.

The fifth condition determines the patient's threshold for understanding speech while raising the signal to noise ratio. A sound bite of speech is played as the background noise is gradually increased (or the SNR is gradually decreased). The patient indicates when the speech is no longer recognizable due to the background noise.

The GUI instructions 132 on the memory 130 of the optimization device 126 provide algorithmic processing that compares the patient's threshold levels 210 for each of the five conditions with the threshold levels for normal hearing listeners. The average levels of a normal hearing listener are based on a database of audiological waves representing speech having a variety of pitches and frequencies against various levels of background noise. If the threshold levels 210 are outside of an acceptable range for each condition, the patient is deemed hearing impaired. An output 212 of the first module 202 is a plurality of ranges of decibel levels the patient has indicated as being at an acceptable level or within an acceptable range per condition.

Figure 4:
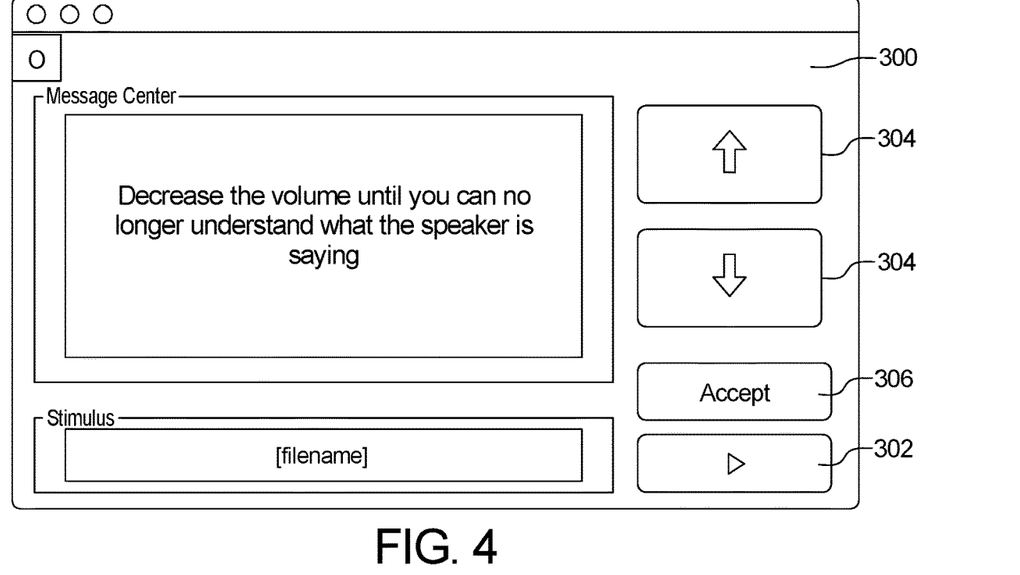
FIG. 4 is a representation of a user interface of an audiometry gathering screen.

FIG. 4 provides an example user interface 300 for collecting audiometry data 208, 210 in the first module 202. By striking the play button 302, the patient triggers the system to provide a sound. The user interface 300 includes arrows 304 that the patient can select to modify the volume. When testing other conditions, the arrows 304 may correspond to variables other than volume as desired or necessitated by the testing condition. The patient clicks on a button 306 labeled "accept" to identify the decibel level that corresponds to the patient's preference based on the conditions above.

The first module 202 may be tailored to test for specific aspects of the cochlear implant NSD 102. For example, the threshold levels for the various conditions are tested for an auditory wave that is a complex summation of many different wave forms that affect a plurality of channels of the electrode array. In some embodiments, the electrode array of the cochlear implant is tested as a collective. In other embodiments, the conditions are tested separately for each channel.

The second module 204 includes a plurality of user interfaces 500, 600, 700 of FIGS. 5-8, respectively, that prompt the patient to select a preferred set of data point(s) corresponding to a specific pitch and/or frequency. The data points initially provided to the patient in the second module 204 are chosen by the second module 204 to be within the specific ranges provided as output 212 from the first module 202. Within the second module 204, one or more user interfaces allow the patient to compare a large number of parameter settings against one another. Through the use of the second module 204, the patient is presented with at least two sound options and asked to select the preferred option. In response to receiving the user's preferred option, the system generates subsequent sound options for testing. The system generates subsequent sound options based on user feedback related to the previous sound options. In a preferred embodiment, statistical analysis of the parameter space enables the system to select subsequent options that are most likely to provide the most meaningful feedback to the system to optimize the efficiency of the iterative selection process. For example, the statistical analysis may include the use of a Gaussian function. Accordingly, the system can automatically explore areas of the parameter space that statistically will provide the most useful information, which results in the most efficient (though not necessarily straight line) path to optimal settings.

Figure 5:
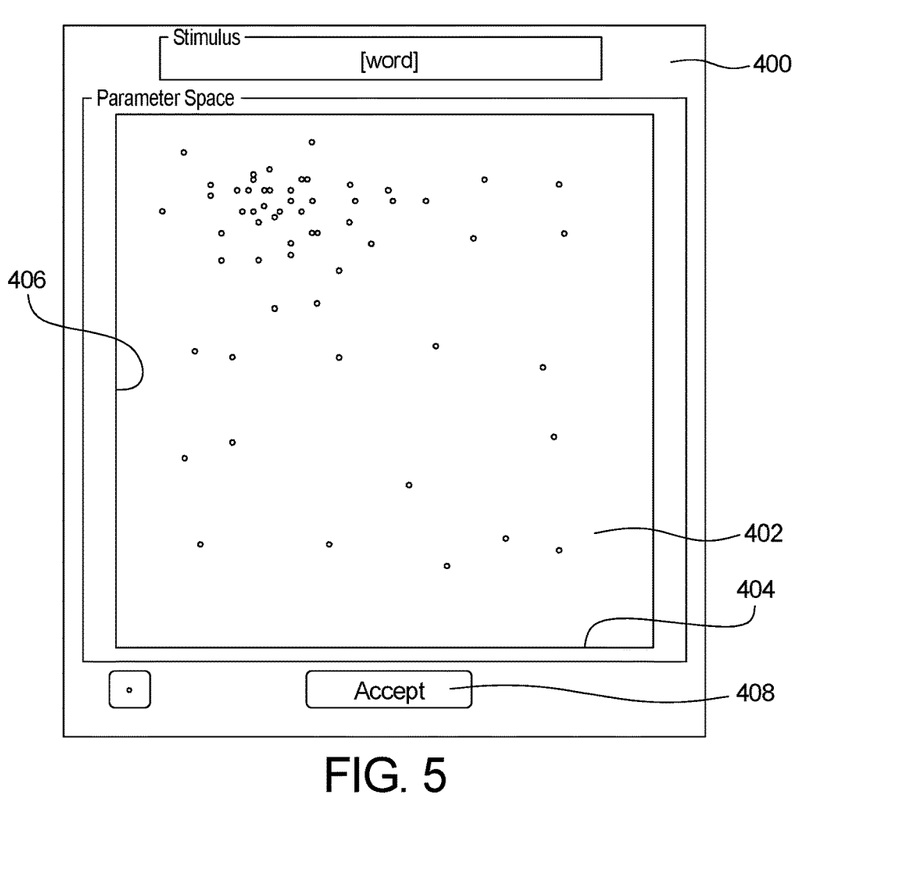
FIG. 5 is a representation of a first user interface of a sound testing screen.

In the first embodiment shown in FIG. 5, the user interface 400 includes an area 402 where each dimension 404, 406 corresponds to a parameter belonging to a function that alters properties of each auditory filter simultaneously. For example, in the embodiment shown in FIG. 5, the parameters associated with the x- and y-axes 404, 406 may be amplification and noise cancellation, respectfully. To begin the tuning process, a user selects a point within the two-dimensional framework, area 402. The parameters are adapted to reflect the settings corresponding to the selected point and a sound is presented to the user. The user then selects another point within the area 402 and the parameters are updated and a further sound is presented to the user using the updated parameters. The user continues selecting points in the area 402, typically clustering within a zone within the area 402, until the user indicates a preferred setting by selecting the "accept" button 408. Once a patient selects a specific space within the area that reflects the preferred sound, that point is accepted and the task is reset with the new word and/or new parameters assigned to the x- and y-axes 404, 406 being appointed. After a plurality of trials have been completed, the points that were accepted are used to compute a best estimate for the set of parameters being optimized and the parameters of the tested NDS 102 are updated accordingly.

Figure 6:
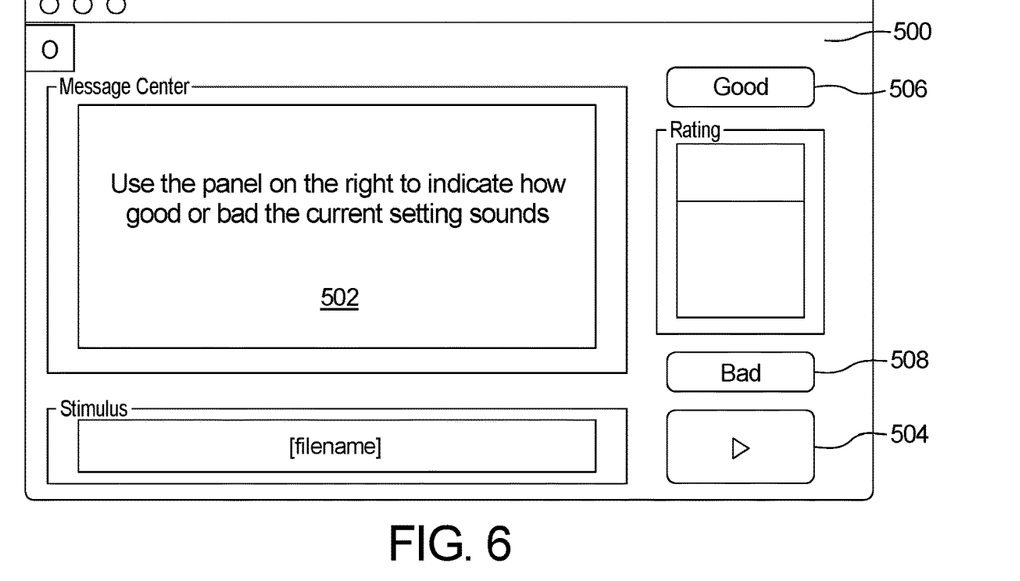
FIG. 6 is a representation of a second user interface of a sound testing screen.
Figure 7:
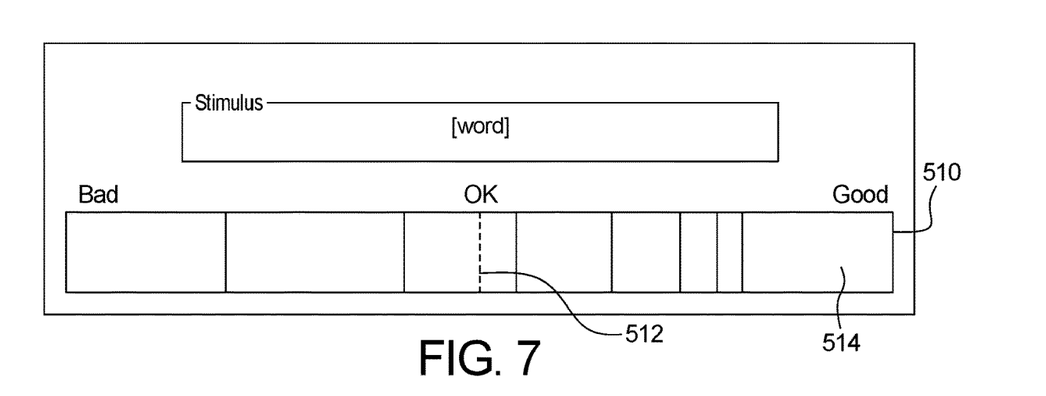
FIG. 7 is a representation of a rating spectrum used in connection with the second user interface of FIG. 6.

In a second embodiment shown in FIGS. 6 and 7, the user interface 500 involves the implementation of an interactive genetic algorithm (IGA) to determine ideal cochlear implant settings. Genetic algorithms use the biological metaphor of evolution and natural selection to construct a set of rules for searching a parameter space for optimal solutions. Genetic algorithms are valued for their flexibility and robustness to local minima due to the high amount of stochasticity utilized during the search process.

In user interfaces 500, 600 the search is initiated by presenting the patient with a small number of device parameters which he or she is asked to rate on a scale relative to each other. In one embodiment, about half of these initial parameters are drawn randomly and uniformly from the parameter space while the other half are drawn at random within a parameter space closely related to the original device settings of the cochlear implant user. The relative ratings for each parameter are then used as inputs for a fitness function which determines which of the settings should be 'selected' to be recombined with other surviving parameters to create 'child' parameters that will then undergo the same pruning and recombination procedure in the next generation. These iterations proceed for about 15-20 generations at which point the majority of the recommendations made are appealing to the user.

For example, in the embodiment 500 shown in FIGS. 6 and 7, the patient is instructed to comply with an instruction presented in the message box 502 of the user interface 500. In the illustrated example, the message box 502 instructs the patient to "Use the panel on the right to indicate how good or bad the current setting sounds." The patient presses the play button 504, which triggers a first sound to be presented to the patient. The patient then selects either of the "good" button 506 or the "bad" button 508 provided adjacent to the message box 502 to provide a rating that corresponds to a point on a rating spectrum 510 shown in FIG. 7. In one example, the length of time that the button 506, 508 is selected corresponds to how strongly the sound is rated. For example, selecting the "good" button 506 for a single click corresponds to a point on the spectrum 510 just to the right of the center 512, while selecting the "good" button 506 for a longer period of time causes the rating to be closer to the "good" end 514 of the spectrum 510. After a plurality of trials have been completed, the ratings provided by the patient are used to compute a best estimate for the set of parameters being optimized and the parameters of the tested NDS 102 are updated accordingly.

Figure 8:
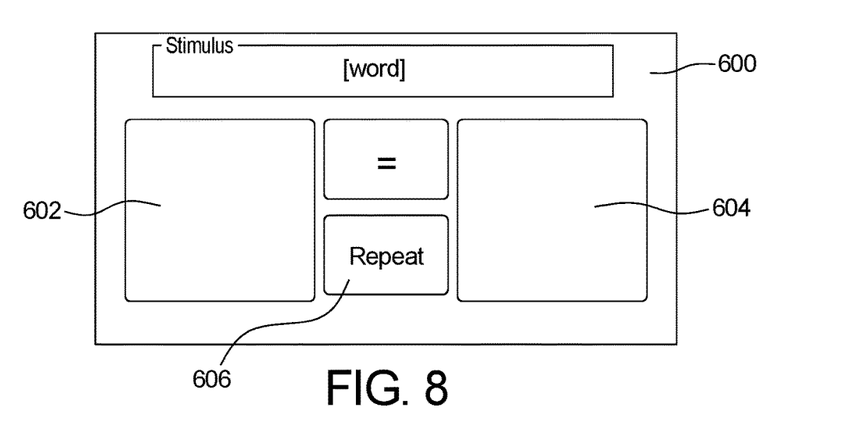
FIG. 8 is a representation of a third user interface of a sound testing screen.

In the third embodiment shown in FIG. 8, the user interface 600 is based on a machine learning framework known as the "dueling bandits" problem. Duels are defined as random comparisons between pairs of parameters where the user determines the 'winner' of each duel. In the user interface 600, two sets of device parameters are drawn at random from the parameter space and played in sequence. The user then selects which of the two settings he or she liked more by pressing a left button 602 or a right button 604 on the user interface 600, with an additional button 606 to repeat the stimuli or ignore them if they both sound unacceptable or similar. The model works under the assumption that the parameters corresponding to the winners of these duels will, on average, be informative in defining a function for recommending sets of parameters that have the highest probability of winning a duel against a parameter generated at random from the parameter space.

The second module 204, and the one or more user interfaces 500, 600, 700 employed, provide specific parameter settings 222 associated with specific sounds or environments.

Referring back to FIG. 2, the third module 206 includes a database 224 on which a reference bank of sounds or environments that identify frequency content associated with each acoustic environment is stored. Using wavelet scattering transforms, a classifier algorithm determines the frequency content of each acoustic environment or sound profile. Alternative methods such as traditional Fourier transforms or spectrograms may be used. Support vector machine (SVM), K-clustering mechanisms, or any type of clustering methods is used to group the information contained in each acoustic environment to create a reference bank of scenarios (i.e., noisy restaurant, commuter train, office, living room, etc.).

Optimized parameter settings 222 associated with specific environments that are output from the second module 204 are provided as input to the third module 206. The optimized parameter settings 222 are matched to clusters within the reference bank of sounds in order to associate the parameter settings with a greater range of environments. Simultaneously, the acoustic environment received on the microphone or auditory input sensor of the cochlea implant or other hearable device is compared with the reference bank of sounds to identify a comparable environment having associated parameter settings. The associated parameter settings 230 are output to the memory of the cochlear implant and automatically factored into the coding strategy of the cochlear implant.

The third module controls the parameter settings of the auditory device or the NSD. In one embodiment, the auditory device 102 includes an auditory device processor 106, an auditory device output mechanism including one or more modifiable parameter settings, and an auditory input sensor 104 that detects an environmental sound and communicates with the auditory device processor 108. The auditory device output mechanism is any output mechanism of an auditory device, such as one or more electrodes 112, 114 of a cochlear implant or a speaker on a hearing aid device. The auditory input sensor 104 may be a microphone positioned on the auditory device. The system also includes a database 123 of reference sound profiles and a plurality of sets of parameter settings, each of which is paired with a corresponding sound profile. The database 123 may be stored directly on the auditory device 192 or remotely on the patient's mobile device or on a remote server.

The auditory device 102 also includes a memory 120 in communication with the processor 108 and including instructions that, when executed by the processor, cause the processor 108 to undertake certain steps that match the environmental sound detected by the auditory input sensor 104 with the reference bank of sounds 123 to identify a comparable environment having associated parameter settings.

More specifically, the processor 108 first receives the environmental sound detected by the auditory input sensor 104 and analyzes a frequency content of the environmental sound. The system may determine the frequency content of the environmental sound by using a wavelet scattering transform to analyze the frequency content of the environmental sound, using a Fourier transform to compute the frequency content of the environmental sound, or any other suitable classifier algorithm to determine the frequency content of the acoustic environment.

The processor 108 compares the frequency content of the environmental sound with the sound profiles stored in the database 123. In response to the comparison, the system selects one of the sound profiles and automatically adjusts the parameter settings of the auditory device output mechanism, such as electrodes 112, 114, to match the set of parameter settings associated with the selected sound profile. Each set of the plurality of sets of parameter settings may include amplification settings, compression settings, and directional noise rejection settings.

Figure 9:
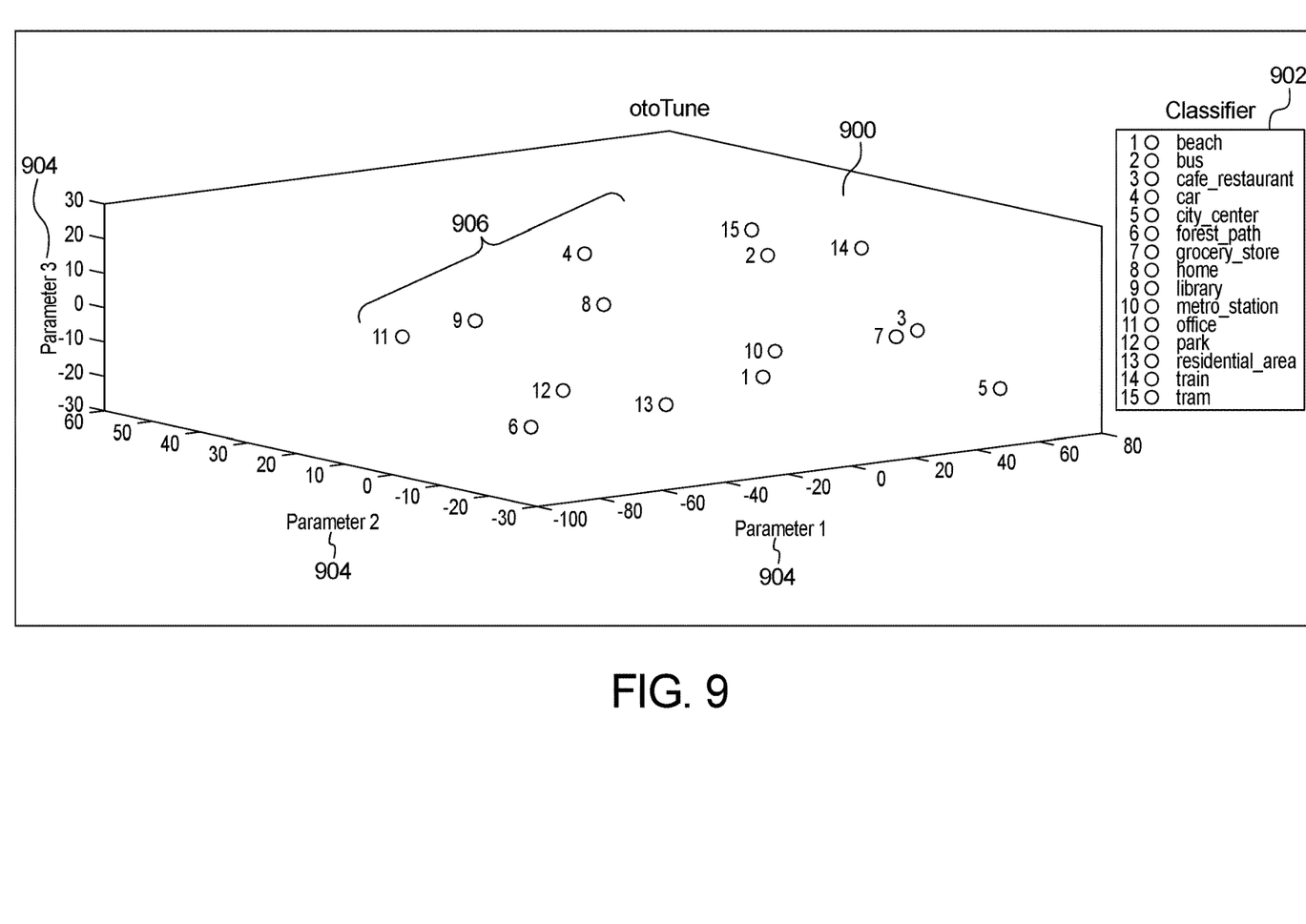
FIG. 9 is a graphic representation of a cluster of sounds of a reference bank.

FIG. 9 is an example of the clustering 900 of different sound profiles 902 based on a plurality of variable parameters 904 to create a database or reference bank of environments and corresponding parameters 906. Example sound profiles of environments include the beach, the bus, the city, the forest, the office, a specific person's voice, such as a parent or child, or other easily characterized or recognizable environments or sounds. The database also includes a set of parameter settings associated with each sound profile. The database may also include parameter settings associated with combinations of recognized environmental sounds, such as, for example, the recognition of a spouse's voice in a home living room environment, which may be a different setting than a child's voice in the same living room setting, which may be different from either of the voices in a dining room setting. During use, the system determines one or more properties of the frequency content of the environmental sound such as, but not limited to, a signal-to-noise ratio, an amplitude range, and a pitch range to recognize the appropriate saved parameters to apply to the system. While only three variable parameters 904 are illustrated in FIG. 9, the clustering software may use many more than three or as few as one parameter to cluster the sounds by similarity.

Each sound profile may also be associated with a stored geolocation. A location sensing mechanism in communication with the auditory device processor determines the present geolocation of the auditory device. After the system selects a sound profile that corresponds to the environmental sound, the processor may further compare a present geolocation of the auditory device output mechanism identified by the location sensing mechanism with the stored geolocations. The geolocation may identify a subset sound profile with an associated set of parameter settings. The geolocation may be particularly useful in maintaining consistency in settings as there are times the positional location will be more stable than the sound environment. As such, it may be the case that based on a given geolocation, the processor is instructed to only choose between a limited number of settings. For example, in the "office" geolocation, the processor may be restricted to choosing between the (i) office desk, (ii) office conference room, and (iii) office cafeteria, settings. A more complex application may include recognizing the geolocation (for example, the user's home), which limits the possible sound profiles from which to choose, then recognizes the background noise (for example, the user's living room with the television on) then recognizes the user's spouse's voice to apply a sound profile matching settings optimized for the user to hear the user's spouse in the user's living room with the television on in the background.

If the acoustic environment received by the microphone does not correspond closely with any of the reference bank of sounds 906, a new environmental setting may be created. In one embodiment, the patient could update his or her parameter preferences for the new acoustic environment either through the hearing device itself or using a mobile application associated with the optimization system of the present application, either through a phone or tablet connected to his or her hearing aid or cochlear implant. In some embodiments, the first and second modules are accessible by the patient through a mobile application on a mobile device. The patient can use the mobile application to tune the parameters to the present environment and store the set of parameter settings associated with the specific environmental sound profile in the database of sound profiles 906.

The patient may also add to the reference bank of sounds associated with specific parameter settings by simulating the sounds during the patient's visit to an audiologist. For example, an audiologist would place a hearing-impaired user in a sound booth and play speech-in-noise or speech-in-babble or even more specific acoustic environments, such as speech on an airplane or speech-in-wind. Using the second module of the optimization system, the patient sets his or her preferred parameters. When the patient is in the real-world environment, all parameter settings are updated based on the current environment's similarity to the previously simulated environments.

The foregoing description merely illustrates the principles of the disclosure. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the disclosure and are thus within the spirit and scope of the present disclosure. From the above description and drawings, it will be understood by those of ordinary skill in the art that the particular embodiments shown and described are for purposes of illustrations only and are not intended to limit the scope of the present disclosure. References to details of particular embodiments are not intended to limit the scope of the disclosure.

We claim:

1. A system for controlling parameter settings of an auditory device for a user comprising:
   an auditory device processor;
   an auditory device output mechanism controlled by the auditory device processor, the auditory device output mechanism including one or more modifiable parameter settings;
   an auditory input sensor configured to detect an environmental sound and communicate with the auditory device processor;
   a database in communication with the auditory device processor, the database including a reference bank of environmental sounds and corresponding sound profiles, each sound profile including an associated set of parameter settings;
   a memory in communication with the auditory device processor and including instructions that, when executed by the auditory device processor, cause the auditory device processor to:
      while the auditory input sensor is detecting a first environmental sound, receive a sound selection from the user, wherein the sound selection is a set of parameter settings, wherein the sound selection is associated with the first environmental sound;
      store a first sound profile in the reference bank corresponding to the first environmental sound, and wherein the set of parameter settings of the sound selection is associated with the first sound profile;
      receive a second environmental sound detected by the auditory input sensor;
      compare the second environmental sound with the reference bank of environmental sounds and corresponding sound profiles stored in the database;
      in response to the comparison, select one of the sound profiles corresponding to the second environmental sound; and
      automatically adjust the parameter settings of the auditory device output mechanism to match the set of parameter settings associated with the selected sound profile.

2. The system of claim 1, wherein the auditory device processor is configured to use a wavelet scattering transform to analyze a frequency content of the second environmental sound.

3. The system of claim 1, wherein the auditory device processor is configured to use a Fourier transform to compute a frequency content of the second environmental sound.

4. The system of claim 1, wherein the auditory device processor is configured to analyze one or more of a signal-to-noise ratio, an amplitude range, and a pitch range of the second environmental sound.

5. The system of claim 4, wherein one or more of the signal-to-noise ratio, amplitude range, and pitch range of the second environmental sound matches one or more of a signal-to-noise ratio, an amplitude range, and a pitch range of one of the sound profiles.

6. The system of claim 1 wherein the auditory device output mechanism is one of an electrode of a cochlear implant and a speaker of a hearing aid.

7. The system of claim 1 wherein the auditory input sensor is one of a microphone of a cochlear implant and a microphone of a hearing aid.

8. The system of claim 1 wherein each set of parameter settings includes amplification settings, compression settings, and directional noise rejection settings.

9. The system of claim 1 wherein each sound profile is associated with a stored geolocation, the system further comprises a location sensing mechanism in communication with the auditory device processor, and wherein the processor is further configured to:

in response to selecting one of the sound profiles, compare a present geolocation of the auditory device output mechanism identified by the location sensing mechanism with the stored geolocations.

10. The system of claim 1 wherein the auditory device processor is further configured to create a further sound selection if none of the sound profiles in the reference bank corresponds to the second environmental sound, wherein the further sound selection is a further set of parameter settings, and wherein the further sound selection is associated with the second environmental sound.

11. A system for controlling parameter settings of an auditory device for a user comprising:

an auditory device processor;

an auditory device output mechanism controlled by the auditory device processor, the auditory device output mechanism including one or more modifiable parameter settings;

an auditory input sensor configured to detect an environmental sound and communicate with the auditory device processor;

a database in communication with the auditory device processor, the database including a reference bank of environmental sounds and corresponding sound profiles, each sound profile including an associated set of parameter settings, including a first set of parameter settings corresponding to a first sound profile and a second set of parameter settings corresponding to a second sound profile;

a memory in communication with the auditory device processor and including instructions that, when executed by the auditory device processor, cause the auditory device processor to:

while the auditory input sensor is detecting a first environmental sound, receive a sound selection from the user, wherein the sound selection is a set of parameter settings, wherein the sound selection is associated with the first environmental sound;

store the first sound profile in the reference bank corresponding to the first environmental sound, and wherein the set of parameter settings of the sound selection is associated with the first sound profile;

receive a second environmental sound detected by the auditory input sensor;

compare the second environmental sound with the first and second sound profiles of the reference bank of environmental sounds stored in the database and, in response to the comparison, select one of the first and second, sound profiles; and automatically adjust the parameter settings of the auditory device output mechanism to match the set of parameter settings corresponding with the selected one of the first and second sound profiles.

12. The system of claim 11, wherein the auditory device processor is configured to analyze a frequency content of the second environmental sound, wherein the auditory device processor is configured to use a wavelet scattering transform to analyze the frequency content of the second environmental sound.

13. The system of claim 11, wherein the auditory device processor is configured to analyze a frequency content of the second environmental sound, wherein the auditory device processor is configured to use a Fourier transform to compute the frequency content of the second environmental sound.

14. The system of claim 11, wherein the auditory device processor is configured to analyze a frequency content of the second environmental sound, wherein the frequency content of the second environmental sound includes one or more properties selected from the group comprising a signal-to-noise ratio, an amplitude range, and a pitch range.

15. The system of claim 14, wherein the one or more properties selected from the group comprising a signal-to-noise ratio, an amplitude range, and a pitch range of the frequency content of the second environmental sound matches one or more properties selected from the group comprising a signal-to-noise ratio, an amplitude range, and a pitch range of one of the sound profiles.

16. The system of claim 11 wherein the auditory device output mechanism is an electrode of a cochlear implant and the auditory input sensor is a microphone of the cochlear implant.

17. The system of claim 11 wherein the auditory device output mechanism is a speaker of a hearing aid and the auditory input sensor is a microphone of the hearing aid.

18. The system of claim 11 wherein each set of parameter settings includes amplification settings, compression setting, and directional noise rejection settings.

19. The system of claim 11 wherein the auditory device processor is further configured to create a further sound selection if none of the sound profiles in the reference bank corresponds to the second environmental sound, wherein the further sound selection is a further set of parameter settings, and wherein the further sound selection is associated with the second environmental sound.

* * * * *